(12) United States Patent
Weber

(10) Patent No.: US 8,043,348 B2
(45) Date of Patent: Oct. 25, 2011

(54) ACUPUNCTURE DEVICE USING A LASER BEAM

(76) Inventor: Michael Weber, Lauenförde (DE)

( * ) Notice: Subject to any disclaimer, the term of this patent is extended or adjusted under 35 U.S.C. 154(b) by 1218 days.

(21) Appl. No.: 11/317,251

(22) Filed: Dec. 27, 2005

(65) Prior Publication Data

US 2007/0208398 A1    Sep. 6, 2007

Related U.S. Application Data

(63) Continuation of application No. PCT/DE2004/000960, filed on May 7, 2004.

(30) Foreign Application Priority Data

Jun. 27, 2003  (DE) .................................. 203 09 976

(51) Int. Cl.
*A61N 5/067* (2006.01)
*A61B 18/20* (2006.01)
*A61B 18/22* (2006.01)

(52) U.S. Cl. .................. 607/89; 607/90; 606/13; 606/16

(58) Field of Classification Search .................... 607/89, 607/90, 156; 600/548; 606/90, 13, 19
See application file for complete search history.

(56) References Cited

U.S. PATENT DOCUMENTS

| | | | | |
|---|---|---|---|---|
| 3,913,582 A | * | 10/1975 | Sharon | 606/19 |
| 4,232,678 A | * | 11/1980 | Skovajsa | 607/89 |
| 4,479,496 A | * | 10/1984 | Hsu | 606/189 |
| 4,653,495 A | * | 3/1987 | Nanaumi | 606/16 |
| 4,779,593 A | * | 10/1988 | Kiernan | 607/65 |
| 5,008,555 A | * | 4/1991 | Mundy | 250/559.22 |
| 5,029,581 A | * | 7/1991 | Kaga et al. | 607/89 |
| 5,131,409 A | * | 7/1992 | Lobarev et al. | 607/156 |
| 5,193,526 A | * | 3/1993 | Daikuzono | 606/15 |
| 5,358,503 A | * | 10/1994 | Bertwell et al. | 606/27 |
| 5,375,596 A | * | 12/1994 | Twiss et al. | 600/424 |

(Continued)

FOREIGN PATENT DOCUMENTS

DE    27 40 969    3/1979

(Continued)

OTHER PUBLICATIONS

Machine translation of D.E. 27 40 969.*

(Continued)

*Primary Examiner* — Roy Gibson
*Assistant Examiner* — Kaitlyn Smith
(74) *Attorney, Agent, or Firm* — Schlesinger, Arkwright & Garvey LLP

(57) ABSTRACT

Acupuncture device uses a laser beam. Acupuncture device is configured for bringing about a suitable treatment relevant to the pain in a patient and so that it is adapted to all aspects of practice, in particular so as to enable easy replacement of laser diodes of different intensity levels or laser modules of different wavelengths and a lasting operating capacity of all its elements. Therefore, the acupuncture device includes the following elements: a control apparatus including several outlets for electrical conductors; several electrical conductors connected to the outlets of the control apparatus; several laser diodes connected to the electrical conductors; and several laser needles which are connected to the laser diodes, so that the laser beam emitted by the laser diodes is injected into the laser needles, and which are designed to contact, through their output region, a patient's body. Device may be used to irradiate blood.

21 Claims, 6 Drawing Sheets

U.S. PATENT DOCUMENTS

| | | | |
|---|---|---|---|
| 5,514,168 A * | 5/1996 | Friedman | 607/89 |
| 6,074,411 A | 6/2000 | Lai et al. | |
| 6,513,962 B1 * | 2/2003 | Mayshack et al. | 362/583 |
| 6,572,637 B1 * | 6/2003 | Yamazaki et al. | 607/89 |
| 6,594,434 B1 * | 7/2003 | Davidson et al. | 385/135 |
| 7,179,278 B2 * | 2/2007 | Schikora | 607/89 |
| 2004/0176825 A1 * | 9/2004 | Vaynberg et al. | 607/89 |
| 2007/0260297 A1 * | 11/2007 | Chariff | 607/89 |

FOREIGN PATENT DOCUMENTS

| | | |
|---|---|---|
| DE | 91 05 621.7 | 10/1991 |
| DE | 295 19 433 U1 | 3/1996 |
| EP | 0 495 757 A1 | 7/1992 |
| WO | 02/40098 A1 | 3/2002 |
| WO | 2005/009538 A2 | 2/2005 |

OTHER PUBLICATIONS

U.S. Appl. No. 11/648,643, filed Jan. 2007, Weber.

International Search Report dated Jan. 5, 2005, in PCT application No. PCT/DE2004/000960, filed May 7, 2004 (2 pages).

International Search Report dated Jan. 5, 2005 in PCT application No. PCT/DE2004/000960, filed May 7, 2004 (3 pages).

* cited by examiner

ACUPUNCTURE DEVICE USING A LASER BEAM

CROSS-REFERENCE TO RELATED APPLICATIONS

This application is a continuation of application no. PCT/DE2004/000960, filed May 7, 2004, which claims the priority of German application no. 203 09 976.1, filed 27 Jun. 2003, and each of which is incorporated herein by reference.

FIELD OF THE INVENTION

The invention relates to an acupuncture device that uses a laser beam. More particularly, the invention relates to an acupuncture device that uses a laser beam injected through laser needles.

BACKGROUND OF THE INVENTION

An acupuncture device using a laser beam is known from WO-02/40098 A1 having a device to generate the laser beam and a connected handle. The handle is provided with an optical fiber that is connected with a laser beam generation device and that contacts a patient's body in the acupuncture process and transmits the laser beam to the body or ensures that the laser beam penetrates the body.

The effectiveness of this device in treating pain is not a matter of dispute; however, the optical fibers made of commercially available plastic fibers that transmit the laser beam from the laser beam generation device to the output section of each handle sometimes cannot handle the continuous load when these devices are used in practice, and sometimes they break and their performance decreases. Another problem with this known device is that the tip forming the output section of the optical fiber in conventional plastic materials quickly becomes comparatively blunt, especially as cosmetics on the patient's skin can be burned into the tip. Furthermore, the macromolecular structures of the plastic fibers denature and degenerate owing to the permanent load which hence decreases the output of the transmitted laser energy.

U.S. Pat. No. 6,074,411 describes a laser device and a laser method that can be used for acupuncture on a patient's body. Individual laser diodes are connected to a controller by means of electrical lines. The laser diodes are within a housing that is adhered to the patient's body.

However, the desired effect of acupuncture pain therapy can fall woefully short with such devices as the laser beam can only penetrate the outermost skin layers and owing to the large area that is irradiated.

DE 90 10 925 U1 describes a device for irradiating blood in which the blood is guided through a glass tube exposed to UV radiation.

OBJECTS AND SUMMARY OF THE INVENTION

An object of the present invention is to create an acupuncture device using a laser beam that is capable of generating an adequate effect for the appropriate treatment of a patient's pain, and that is also suitable from all vantage points of practical use, especially the easy exchangeability of the laser diodes or laser modules with different wavelengths and diode strengths, and long service life of all the elements.

This object is achieved according to the invention by the features set forth herein.

The glass fiber needles or plastic fiber needles analogous to glass fibers (subsequently termed "optical fibers" for short throughout) into which the laser beam emitted by the laser diodes is coupled ensure that the laser beam is introduced into the patient's body with a very high energy density owing to the provided focus of the laser beam and direct contact between the laser needles and the body to ensure a very high efficiency of the device according to the invention. By using glass fibers or plastic fibers analogous to glass fibers (subsequently termed "optical fibers" for short throughout) for the laser needles that contact the patient's body, the device is ensured a very long life as the laser needles are insensitive to the damage from any foreign bodies. Furthermore, the laser diodes are easily accessible for servicing, repair, and exchange as they are not arranged inside the control device.

In one embodiment of the invention, the laser diodes are on the head of the laser needle. The short laser needles form a relatively short section of the entire conduit proceeding from the controller as the remaining section that must be guided from the controller to the patient's body is formed by the power supply lines. These power supply lines can be very flexible in a known manner so that there is no danger of them breaking. For this reason, the device according to the invention is highly suitable for practical use. As the laser diode sits directly on the short laser needle, in principle there are no power losses from the generated laser beam.

In another embodiment of the invention, the power lines are guided in a bundle in or on a holding arm from the controller to a module plate on the end of the holding arm. The power lines of the bundle are separated in or on the module plate, and a laser module having a driver chip and a laser diode are connected to the ends of the power lines on the module plate, and the laser modules are connected to the laser needles via suspended optical fibers protected by a sheath. The laser needles can be configured as a single piece with the optical fibers, or they can be connected to them via an optical coupling element. Even when optical fibers are between the laser diodes and the laser needles in this embodiment, the laser beam is transmitted into the patient's body at a high energy density as optimum conduction conditions exist for the laser beam in the optical fiber. Another advantage of this embodiment results when the laser modules are in the peripheral area of the modular plate, and a fan is in the center. This effectively cools the laser modules whose overheating frequently causes failure of the state-of-the-art devices.

In another embodiment of the invention, it is advantageous when the power lines are connected to the respective laser diodes or laser modules by means of respective plug-in connections. This allows the different laser needles and/or laser diodes or laser modules connected to the needles to be easily exchanged and hence adapted to the respective usage without requiring special service personnel. The user can create an individual set of laser needles in this manner. In the unlikely event that one of the laser needles wears out or is defective, it can be quickly and easily exchanged. When optical fibers are arranged between the laser modules and laser needles, it is also advantageous for there to be a plug-in connection between the laser model and optical fiber which enables the laser needles to be exchanged without simultaneously exchanging the laser modules.

As the controller only has to transmit current pulses to the laser diodes, it can be advantageously configured very small so that it is suitable for mobile use and, if necessary, can also be affixed to the body of a treated patient so that the patient's body can move with the controller. This is particularly advantageous when using the device according to the invention on children or animals.

In an advantageous development of the invention, the laser needles can be protected even more from damage by coating the laser needles with plastic sheaths.

If the laser needles and/or a core of the laser needles narrow(s) from the laser diode towards its output section in another embodiment of the invention, this increases the energy density at the output of the laser needles to further stimulate the patient's body. Alternatively, when the laser needles narrow in this manner, it is of course also possible to use the laser diodes with less output to attain the same stimulus as with laser needles that do not narrow in this manner.

The power lines are very easy to handle when the power lines are connected to the controller by means of respective plug-in connections especially when they become defective and need to be exchanged.

To enable mobile use of the device according to the invention, the controller can be operable with a battery in another advantageous embodiment of the invention.

In another embodiment of the invention, the laser needles can be surrounded by a current-conducting sheath that is supplied with current from the controller.

With such a sheath supplied with current, the stimulus of the patient's body from the laser beam can be increased to better treat the pain.

A device for irradiating blood is described herein. The use of the laser beam acupuncture device according to the invention for such a device to irradiate blood has proven to be quite feasible in practice. By irradiating the blood with a laser beam, the white corpuscles are activated much more than with the known irradiation method using UV radiation. This produces greater immune stimulation. Furthermore, the utilized laser needles are advantageously very easy to dose.

Additional advantageous embodiments and developments of the invention can be found as described herein, and as set forth in the schematically portrayed exemplary embodiments in the drawings, and in the related text, and which are not intended to be limiting.

DETAILED DESCRIPTION OF THE INVENTION

Figure 1:
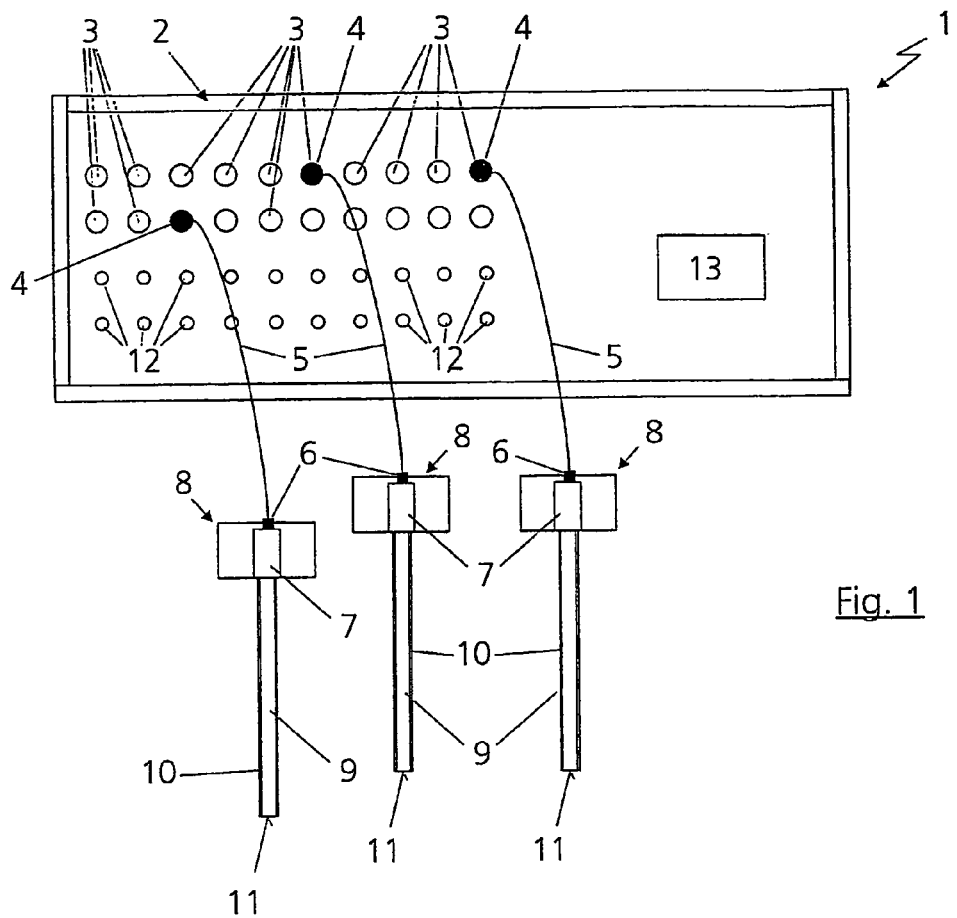
FIG. 1 shows a first embodiment of the acupuncture device using a laser beam according to the invention.

FIG. 1 shows a schematic representation of an inventive device 1 for acupuncturing a part of an unillustrated patient's body using a laser beam. The device 1 has a controller 2 that is provided with several outputs 3. In the present case, there are a total of twenty outputs 3; however, any number of outputs 3 can be provided. Connected to the outputs 3 via respective plug-in connections 4 are power lines 5 that are supplied with current, especially a weak current, from the controller 2. The voltage applied to the power line 5 and the current strength can be adjusted using a regulator (not shown) on the controller 2.

A laser diode 7 capable of transmitting a laser beam is connected via respective plug-in connections 6 to each power line 5. The connection between the laser diodes 7 and the power line 5 can also be established by soldering the two parts together. Each individual laser diode 7 is in a handle 8 and is connected to one of respective laser needles 9, for example, by adhesion. The present exemplary embodiment shows only three handles 8 with respective laser needles 9, the associated laser diode 7 and power line 5; however, corresponding laser needles 9 can be connected to all the outputs 3 of the controller 2 to simultaneously treat several acupuncture points on the patient's body.

The laser needles 9 are surrounded with respective plastic sheaths 10 to protect them and are provided to contact the patient's body at their respective output section 11. The laser beam transmitted by the laser diodes 7 is injected or coupled into the laser needles through the direct connection to the laser needles 9, and the laser beam is guided into the patient's body essentially without loss.

In order to amplify the laser beam transmitted by the laser diode 7, the laser needles 9 can narrow from the respective laser diode 7 to their output section 11 (not shown). The narrowing of the laser needles 9 is proportional to the amplification of the laser beam. In this context, the laser diodes 7 can have different outputs, for example ranging from 50 to 200 mW. In addition to the different outputs, the individual laser diodes 7 can also have different wavelengths to make them suitable for different uses on the same patient. Furthermore, it is also possible to modulate the frequency of the laser beam transmitted by the laser diodes 7 by using the controller 2 to pulse the laser beam and hence stimulate different kinds of tissue.

The controller 2 has an intensity display 12 for each output 3 that shows the intensity of the laser beam transmitted by the laser diodes 7 in digital form. Furthermore, the controller 2 is equipped with a photometer 13 that measures the intensity of the laser beam in the output section 11 of the laser needle 9, for example to check the proper functioning of the laser needles. To do this, the respective laser needle 9 only needs to be held in front of the photometer 13.

The size of the controller 2 can enable it to be affixed with holding devices (not shown) to the body of the treated patient. To be completely independent from the power network, the controller 2 can also be operated by a battery (not shown). Furthermore, the controller 2 can have a timer to control it.

Figure 2:
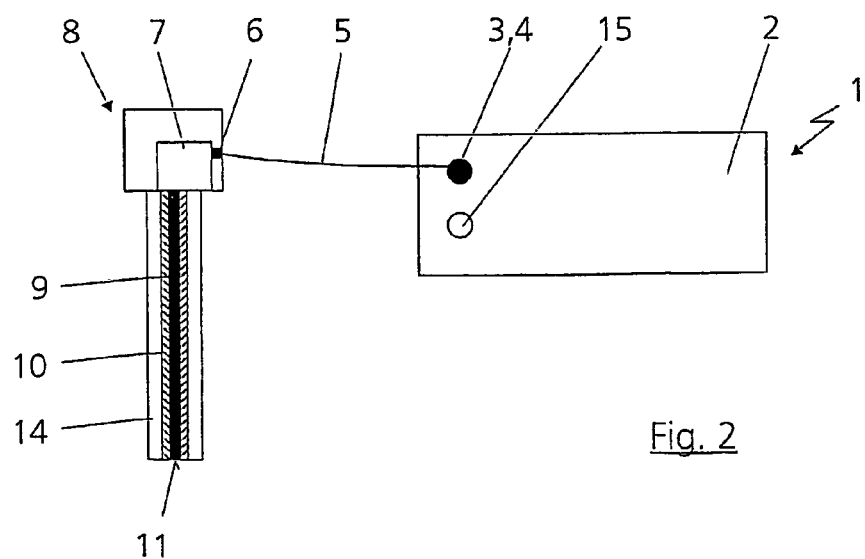
FIG. 2 shows a second embodiment of the acupuncture device using a laser beam according to the invention.

FIG. 2 shows another embodiment of the device 1 where the laser needle 9 is surrounded by a plastic sheath 10 and another sheath 14 supplied with current via the respective power line 5 to provide stimulation by current as well as stimulating the tissue by the laser beam and hence enhance the effect of the laser beam. The plastic sheath 10 also serves to protect the laser needle 9 and insulate the laser needle from the current-bearing sheath 14. The sheath 14 may consist of a conductive material such as steel or copper and can be surrounded by another plastic sheath (not shown) for additional insulation.

The current-bearing sheath 14 can also be used to stimulate the acupuncture point by electrical and possibly additional optical stimulus to locate it with a pulse reflex. This allows the acupuncture points to be more precisely determined, and active points can be more reliably found.

Furthermore, the current-bearing sheath 14 can also be used to more precisely locate the acupuncture point by measuring skin resistance.

In principle, it is also possible to connect a known diagnostic needle that does not generate a laser beam to locate the acupuncture points at one of the outputs 3 of the controller 2.

The controller 2, of which only one of the outputs 3 is shown in the present case, has a regulator 15 that is used to adjust to the intensity of the current fed to the sheath 14.

Figure 3:
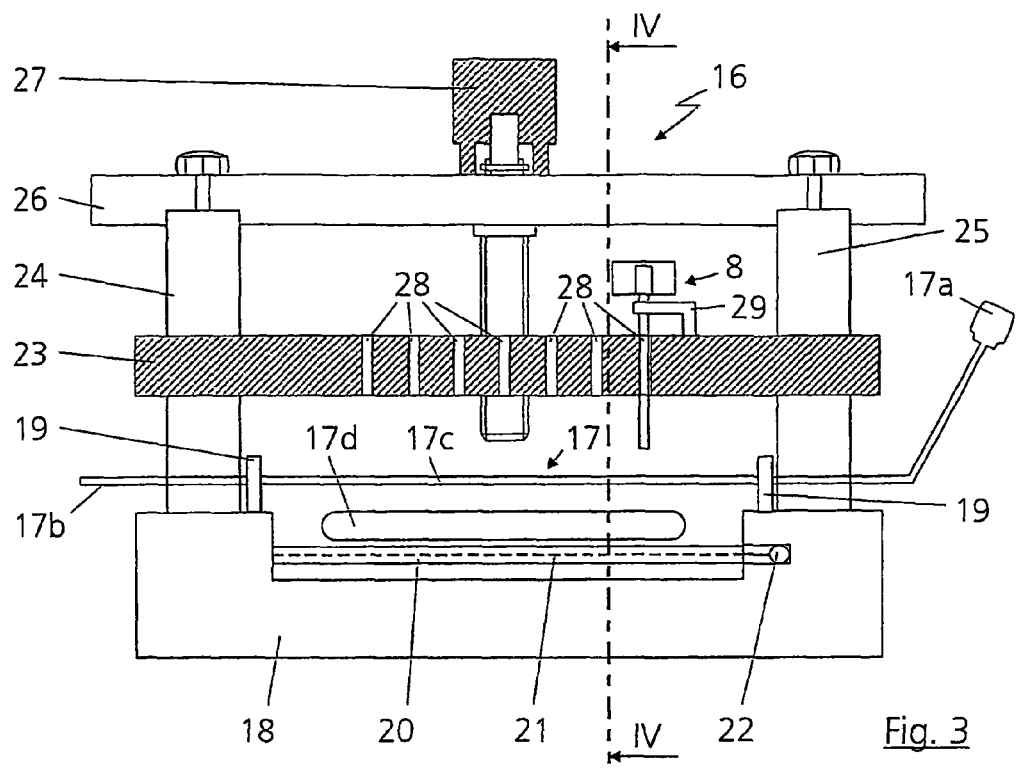
FIG. 3 shows a side view of a device according to the invention for irradiating blood.
Figure 4:
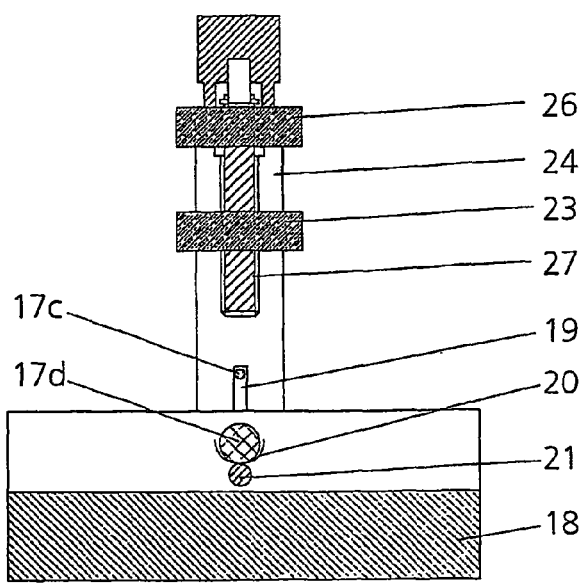
FIG. 4 shows a section taken along line IV-IV of FIG. 3.

FIGS. 3 and 4 also schematically represent a device 16 for irradiating blood in a container 17. The device 1 shown in FIGS. 1 and 2, especially in FIG. 1, is suitable for irradiating the blood in the container 17.

There are two options, both of which are shown in FIG. 3, of irradiating blood or configuring the container 17 and arranging it in the device 16. In the first procedure, approximately 200 mL of blood is withdrawn from the patient (in a manner not shown) in a closed system. The blood is collected in a vacuum bottle 17a to which additional oxygen can be added. This blood enriched with oxygen is then returned to the patient and hence retransfused via a tube system 17b. The container 17 is incorporated in the tube system 17b, e.g. in the form of a thin glass tube 17c that is irradiated with a laser beam from the laser needles 9 as described below. The thin glass tube 17c can be tightly connected to the tube system 17b with silicon connectors, etc. In this procedure, the blood flows while it is being irradiated.

The controller 2 is not shown in FIGS. 3 and 4. The described device 16 can be surrounded by a housing (not shown) or a covering.

An intraversal and extraversal blood radiation device can also be operated as an independent device, i.e. with an integrated controller that controls the swapped laser needles, and the laser needles externally or internally irradiate the blood via an additionally connected sterile single-use laser catheter.

In the other procedure, the drawn blood is placed in a somewhat larger glass tube 17d that is held by the device as described below and also irradiated in the device. Then the blood must be withdrawn from the glass tube 17d and reintroduced into the patient for example by injection.

The device 16 has a base plate 18 on which two holders 19 are located that hold the tube 17b with the thin glass tubes 17c. Below the thin glass tube 17c, a troughlike channel 20 more clearly portrayed in FIG. 4 in which a shaft 21 rotates also serves to hold the glass tube 17d. The shaft is driven by a drive 22, such as an electric motor. As the shaft 21 rotates, the glass tube 17d in the channel 20 rotates in an opposite direction to move the blood in the glass tube 17d while it is being irradiated. Unillustrated rubber rings around the circumference of the channel can support this rotation. Despite the portrayal of both procedures or options to irradiate blood in FIG. 3, it should be clear that either the thin glass tube 17c or the glass tube 17d can be used.

Above the base plate 18 is a holder plate 23 that is mounted on two columns 24 and 25 and can move in relation to the base plate 18. The two columns 24 and 25 are held on the side opposite the base plate 18 with a connecting support 26. The holder plate 23 is moved in relation to the columns 24 and 25 with a set screw 27 held to the connecting support 26 and guided by an unillustrated central thread in the holder plate 23.

The intensity of the laser beam in relationship to the blood can be changed by adjusting the holder plate 23. Furthermore, by adjusting the holder plate 23, the height of the optical fiber needle 9 can be adjusted relative to the thin glass tube 17c or the glass tube 17d as they are stacked on each other and hence have a different axial distance from the holder plate 23.

The holder plate 23 has several through holes 28 in which the handles 8 with the laser needles 9 can be placed. FIG. 3 only shows one of the glass fiber needles 9. Fastening elements 29 are provided to hold the handles 8 or the laser needles 9 to the holder plate 23, and the fastening elements can be screwed to the holder plate 23.

It is also possible for the holder plate 23 to not be adjustable and move the individual laser needles 9 within the holes 28 relative to the holder plate 23. Furthermore, the base plate 18 can be adjustable in relation to the holder plate 23 or laser needles 9.

Figure 5:
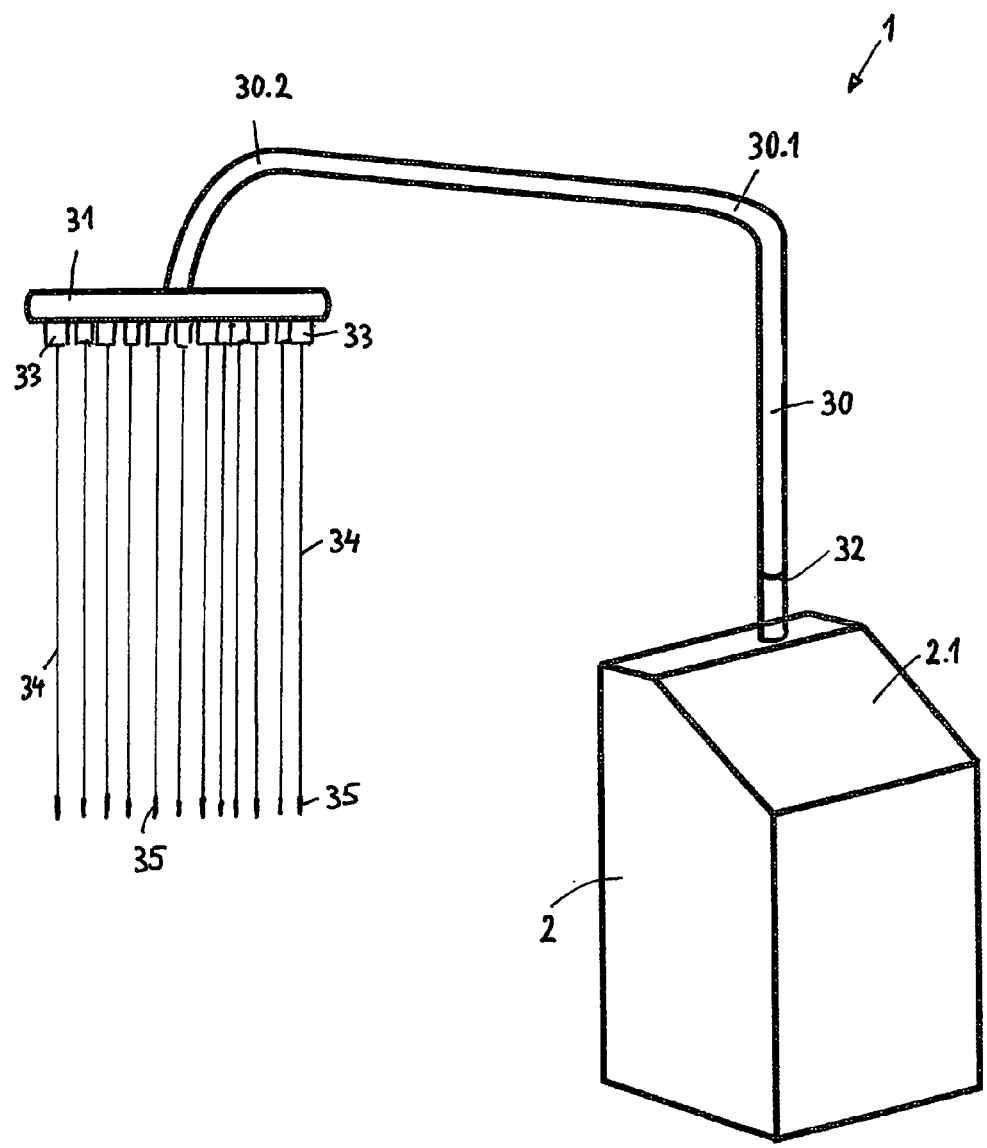
FIG. 5 shows another embodiment of the device according to the invention.

The device 1 shown in FIG. 5 for acupuncturing a patient using a laser beam has a controller 2 with the same functions as the controllers explained with reference to FIGS. 1 and 2. The housing of the controller 2 has a control console 2.1. From the top of the controller 2, a hollow bearing arm 30 extends upward that transitions at a first knee 30.1 into a more or less horizontal section, and then starts downward at a second knee 30.2 and ends in a module plate 31. The holding arm 30 is more or less configured like a gallows. In its vertical part, it has a swivel joint 32 shortly above the controller 2 so that the part of the holding arm 30 above the swivel joint 32 can be swung at least within limits in relation to the controller 2. At least one area of the holding arm 30 is bendable. This can for example be knee areas 30.1 and/or 30.2.

Running within the holding arm 30 is a bundle of power lines 5; one end of the power lines is connected to the controller 2 and controlled via the control console 2.1. The power lines 5 are guided in the holding arm 30 to the module plate 31, and are separated there. Their ends at that location are connected to a laser module 33 which is connected via suspended optical fibers 34 to laser needles 35. The optical fibers 34 are protected by an unillustrated sheath. Holding arm 30 is sufficiently strong, as shown in FIG. 5, so that laser module 31 and optical fibers 34 are suspended thereby.

The configuration and arrangement of the laser modules 33 on the module plate 31 will be further explained below with reference to FIG. 6.

Figure 6:
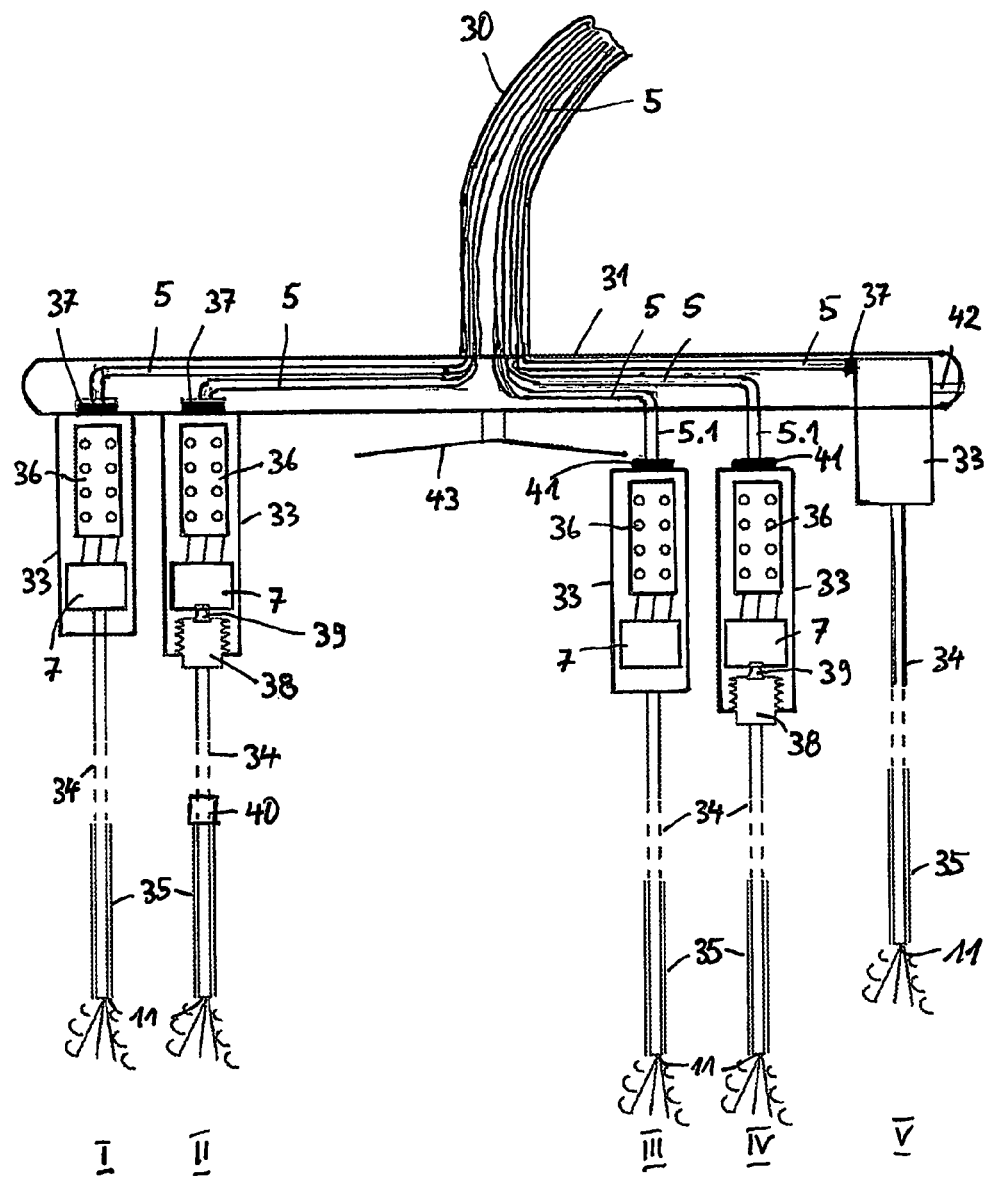
FIG. 6 shows an enlargement of detail A from FIG. 5.

FIG. 6 shows different exemplary options I-V of a connection between the power lines 5 and the laser modules 33, or between the laser modules 33 and the optical fibers 34. In every case, the laser modules 33 consist of a laser diode 7 and a driver chip 36. In cases I and II, the laser modules are connected via plug-in contacts 37 provided in the module plate 31 to the power lines 5 assigned to them. To exchange the laser modules 33, they are simply unplugged from the module plate 31, and new laser modules 33 are inserted. Repairs can be easily done in this manner, or the operator can exchange laser modules 33 with different wavelengths and diode strengths. In case I, the optical fiber 34 and the laser needle 35 connected to the laser module 33 are also exchanged along with the laser module as the optical fiber 34 is glued into the laser module 33. In case II, this is avoided by providing an optical plug 38 between the laser module 33 and the optical fiber 34. To connect the laser module 33, the optical fiber 34 is simple plugged into this plug 38. An optical coupling element 39 is used for coupling with the laser diode 7. In case II, the laser module 33 and optical fibers 34 can be separately exchanged. This system can be further elaborated by providing an additional plug-in connection 40 with an optical coupling between the optical fiber 34 and laser needle 35. In this case, the laser needle 35 can be separately exchanged. The laser diode 7 can also be screwed in separately into the metal housing of the laser module 33 so that it can be exchanged by itself when there is an isolated defect. Screwing in the laser diode 7 into the housing of the laser module 33 and providing a close contact with the housing metal allows the heat generated by the laser diode 7 to be effectively drawn off.

Cases III and IV differ from cases I and II in that the laser module 33 is not inserted into the module plate 31; instead, the electrical lines 5 extend downward a short distance out of the module plate 31. Plug-in connections 41 are also provided between the ends of the power lines 5 and laser modules 33.

In case V, the laser modules 33 are inserted into a corresponding opening in the module plate 31 and fastened with set screws 42. In this case, the module plate 31 is a metal block. The contact of the laser module 33 with this metal block allows heat to flow from the laser model 33 into the metal block.

In addition to or instead of this cooling method, a fan 43 can be provided in the central area of the module plate 31. The laser modules 33 are then in the peripheral area on the module plate 31 and hence surround the fan 43. This configuration is best seen in the drawing in FIG. 7. The fan 43 powerfully cools the strongly heated laser module 33 and thereby substantially increases its service life.

Figure 7:
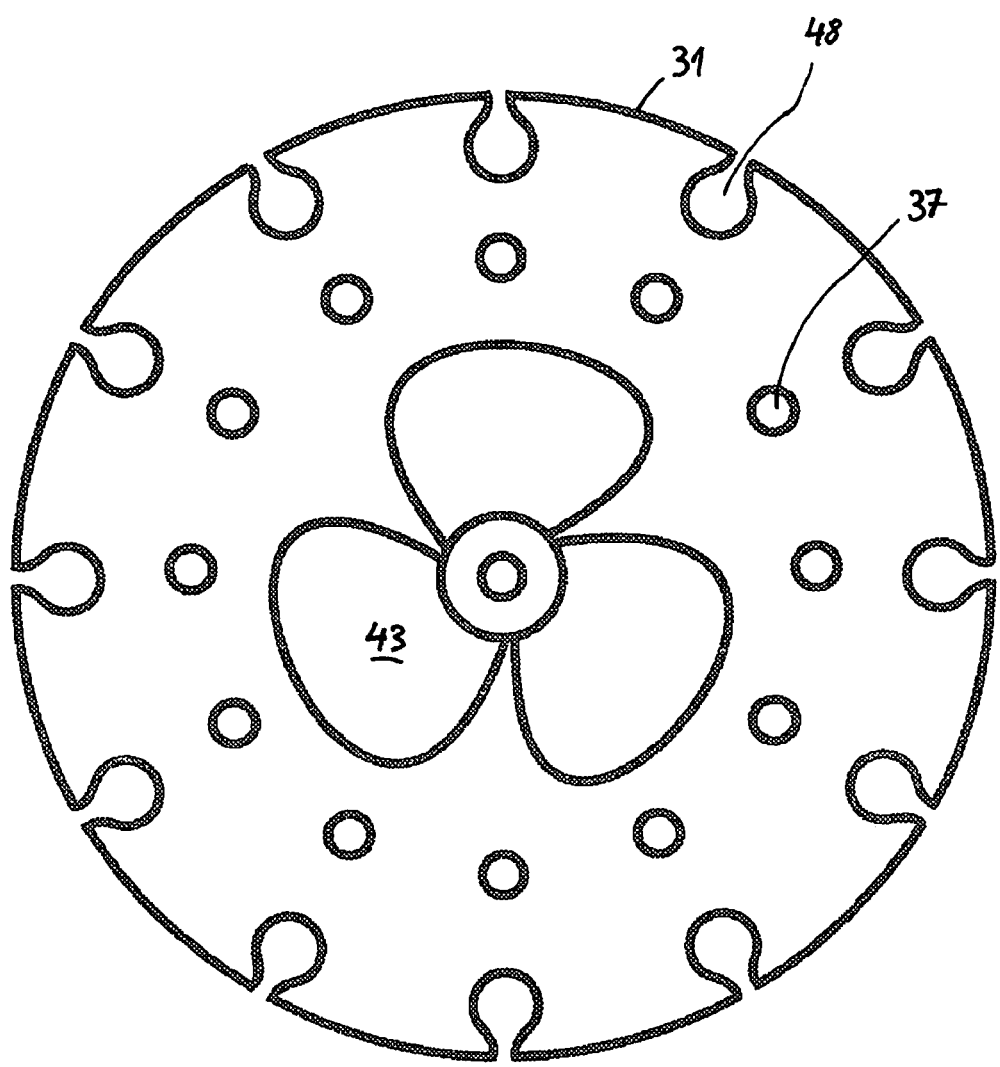
FIG. 7 shows view from below of detail A from FIG. 6.

The drawing in FIG. 7 shows cut-outs 48 provided in the edge of the module plate 31. These are for suspending the laser needles 35 when they are not needed.

In cases I to V, the laser needles 35 can be configured as combined laser electro-needles. The power lines in the sheath of the optical fibers leading from the controller 2 to the laser electro-needles additionally protect the optical fibers from breaking.

To affix the laser needles 35 to a patient's skin 46, single-use sheaths 44 made of economical material such as cardboard or plastic are provided. The sheaths have a shaft 44.1 that is shoved onto laser needles 35 and grips the needle by friction. The shaft 44.1 transitions into a wider base 44.2 that adheres to a patient's skin 46.

Figure 8:
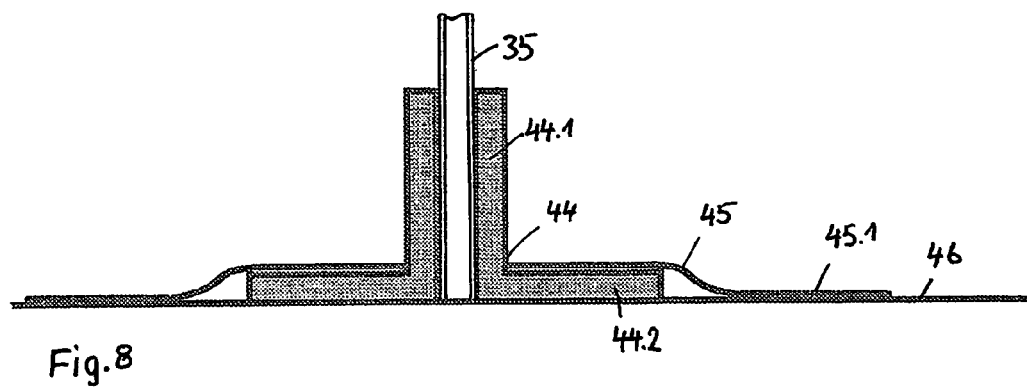
FIG. 8 shows a first option for fixing a laser needle to the body of the patient.

In the exemplary embodiment of FIG. 8, the adhesive connection is created by a bandage with a central hole 45. It is shoved over the shaft 44.1 and lies on the top of the base 44.2. An area 45.1 of the bandage with the central hole 45 extending over the base 44.2 of the disposable sheath 44 is for adhering to human skin 46. The disposable sheath 44 and bandage with the central hole 45 can be provided on removable film as a prefabricated unit.

Figure 9:
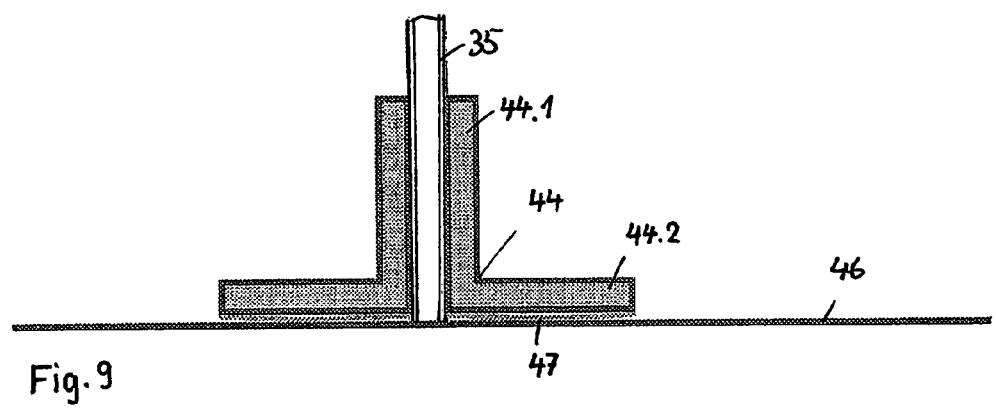
FIG. 9 shows a second option for fixing a laser needle to the body of the patient.
Figure 10:
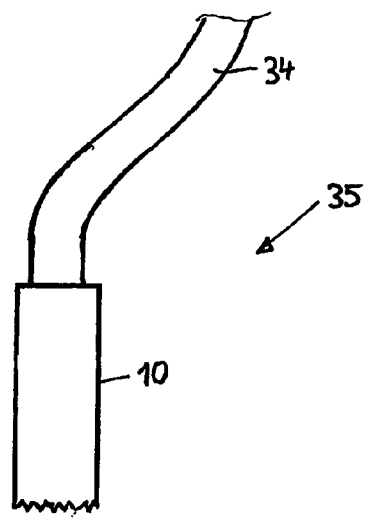
FIG. 10 shows an enlargement of a plastic sheath surrounding a laser needle.

In the exemplary embodiment of FIG. 9, an adhesive ring 47 is provided on the bottom of the base 44.2 that provides the adhesive connection with human skin 46. The disposable sheath 44 and the adhesive ring 46 can also be provided as a unit on removable film.

In another embodiment of the invention, the plastic sheath 10 encasing the lower end of the laser needle 9, 35 is provided with small teeth. This improves the grip of the laser needle 9 to difficult body parts such as an ear.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention or limits of the claims appended hereto.

The invention claimed is:

1. An acupuncture device using a laser beam, comprising:
a) a controller including outputs configured for receiving power lines;
b) power lines connected to the outputs of the controller;
c) laser diodes connected to the power lines, the laser diodes being configured for emitting a laser beam;
d) laser needles having respective output sections, and being configured for contacting a patient's body at their output sections;
e) the laser needles being connected to the laser diodes, and being configured for transmitting the laser beam emitted by the laser diodes and injected into the laser needles when contacting a patient's body at the respective output sections, in use;
f) one of the laser needles being surrounded by a current-conducting sheath configured for being supplied with current from the controller;
g) the power lines being guided in a bundle by a holding arm from the controller to a module plate provided on an end of the holding arm at which the power lines of the bundle are separated;
h) a laser module including a driver chip and one of the laser diodes being connected to an end of one of the power lines by the module plate;
i) the laser module being connected via a suspended optical fiber protected by a sheath to the respective one of the laser needles; and
j) the holding arm being configured as a gallows, the holding arm including a substantially vertical part, a substantially horizontal part, a swivel joint, a bendable knee, and the holding arm being sufficiently strong for supporting the module plate and the optical fiber.

2. Device according to claim 1, wherein:
a) the laser diodes are provided on a head of one of the laser needles.

3. Device according to claim 1, wherein:
a) the laser module is provided on a periphery of the module plate; and
b) a fan is provided in a center region for cooling the laser module.

4. Device according to claim 1, wherein:
a) cutouts are provided in an edge of the module plate and configured for hanging the laser needles.

5. Device according to claim 1, wherein:
a) the end of one of the power lines extends a distance out of the module plate.

6. Device according to claim 1, wherein:
a) the holding arm is movable at least one section of its length.

7. Device according to claim 1, wherein:
a) the power lines are connected to one of the laser diodes and to the laser module with a respective plug-in connection.

8. Device according to claim 1, wherein:
a) the power lines are connected to the controller with plug-in connections.

9. Device according to claim 1, wherein:
a) one of the laser needles and a core of one of the laser needles narrows from the respective laser diode to its output section.

10. Device according to claim 1, wherein:
a) a frequency of the laser beam can be modulated with the controller.

11. Device according to claim 1, wherein:
a) the respective laser diodes have one of different wavelengths and different outputs.

12. Device according to claim 1, wherein:
a) the controller includes a photometer configured to measure the intensity of the laser beam in the output section of one of the laser needles.

13. Device according to claim 1, wherein:
a) the controller is operable with a battery.

14. Device according to claim 1, wherein:
a) one of the laser needles is coated with a plastic sheath.

15. Device according to claim 14, wherein:
a) a bottom end of the plastic sheath includes teeth.

16. Device according to claim 1, wherein:
a) a disposable sheath including one of cardboard and plastic having a shaft is provided, the disposable sheath being shovable onto one of the laser needles and gripping the laser needle by friction, in use; and
b) the disposable sheath transitioning into a wide base configured for adhering to a patient's skin, in use.

17. Device according to claim 16, wherein:
a) an adhesive layer is provided on a bottom portion of the base.

18. Device according to claim 16, wherein:
a) a bandage with a central hole is configured for being shoved on the shaft, in use, and an adhesive layer of the bandage extends over a side of the base.

19. Device according to claim 1, wherein:
a) a container is provided, the container being configured for containing blood; and
b) at least one of the laser needles is configured for transmitting the laser beam emitted by the laser diodes and injected into the laser needles into the container when the container contains blood, in use, for irradiating the blood contained in the container.

20. Device according to claim 19, wherein:
a) a distance between the one of the laser needles and the container is adjustable.

21. Device according to claim 20, wherein:
a) the container is provided on a base plate, and the one of the laser needles is provided on a holder plate, the holder plate being movable in relative to the base plate.

* * * * *